United States Patent [19]

Uhr et al.

[11] Patent Number: 5,521,211

[45] Date of Patent: May 28, 1996

[54] SUBSTITUTED 2-ARYLPYRROLES

[75] Inventors: Hermann Uhr, Leverkusen; Christoph Erdelen, Leichlingen; Ulrike Wachendorff-Neumann, Monheim; Wilhelm Stendel, Wuppertal, all of Germany

[73] Assignee: Bayer Aktiengesellschaft, Leverkusen, Germany

[21] Appl. No.: 335,876

[22] PCT Filed: May 17, 1993

[86] PCT No.: PCT/EP93/01231

§ 371 Date: Nov. 10, 1994

§ 102(e) Date: Nov. 10, 1994

[87] PCT Pub. No.: WO93/24001

PCT Pub. Date: Dec. 9, 1993

[30] Foreign Application Priority Data

May 29, 1992 [DE] Germany .................. 42 17 722.7

[51] Int. Cl.$^6$ ................... A61K 31/395; C07D 207/30
[52] U.S. Cl. ................ 514/426; 514/427; 548/524; 548/557; 548/561; 548/562
[58] Field of Search ................ 548/561, 524, 548/557, 562; 514/426, 427

[56] References Cited

U.S. PATENT DOCUMENTS

| | | | |
|---|---|---|---|
| 4,929,634 | 5/1990 | Herman et al. | 514/426 |
| 5,010,098 | 4/1991 | Brown et al. | 514/426 |
| 5,030,735 | 7/1991 | Addor et al. | 548/531 |
| 5,118,816 | 6/1992 | Doehner, Jr. et al. | 548/565 |
| 5,130,328 | 7/1992 | Kameswaran | 514/426 |
| 5,192,794 | 3/1993 | Uhr et al. | 514/422 |
| 5,194,630 | 3/1993 | Kameswaran et al. | 548/561 |
| 5,233,051 | 8/1993 | Uhr et al. | 548/526 |

FOREIGN PATENT DOCUMENTS

| | | | |
|---|---|---|---|
| 0312723 | 4/1989 | European Pat. Off. | 548/561 |
| 0347488 | 12/1989 | European Pat. Off. | 548/561 |
| 0358047 | 3/1990 | European Pat. Off. | 514/426 |
| 0492171 | 7/1992 | European Pat. Off. | 514/422 |
| 0515941 | 12/1992 | European Pat. Off. | 514/426 |
| 0530147 | 3/1993 | European Pat. Off. | 548/526 |
| 0530515 | 3/1993 | European Pat. Off. | 548/565 |

OTHER PUBLICATIONS

CA 117:212309s Preparation of . . . agents. Kameswaran et al., p. 823, 1992.
CA 120:217699r Preparation of . . . pesticides. Uhr et al., p. 1085, 1994.

Primary Examiner—Joseph K. McKane
Attorney, Agent, or Firm—William C. Gerstenzang; Sprung Horn Kramer & Woods

[57] ABSTRACT

Novel substituted 2-arylpyrroles of the formula (I) are described

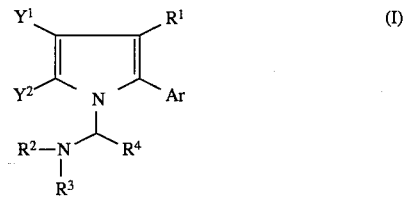

in which $R^1$, $R^2$, $R^3$, $R^4$, Ar, $Y^1$ and $Y^2$ have the meaning given in the description, as is a process for their preparation.

The novel 2-arylpyrroles are used as agents for combating pests.

6 Claims, No Drawings

SUBSTITUTED 2-ARYLPYRROLES

This application is a 371 of PCT/EP93/01231 filed May 17, 1993.

The present invention relates to novel substituted 2-arylpyrroles, intermediates for their preparation and their use for combating animal pests, in particular insects, arachnids and nematodes, encountered in agriculture, in forestry, in the protection of stored products and of materials, and in the hygiene field.

It is known already that structurally similar cyanopyrroles are effective as molluscicides, fungicides and insecticides (see in this context e.g. EP-A 0 347 488, EP-A 0 358 047, EP-A 0 312 723, DE-A 4 117 752). However, the efficacy and range of effect of these compounds is not always completely satisfactory, in particular when using low quantities and concentrations.

Novel substituted 2-arylpyrroles of the general formula (I) have now been found

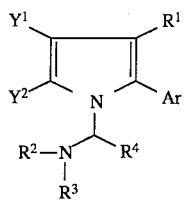

in which
$R^1$ represents cyano or nitro,
$R^2$ and $R^3$, independently of each other, represent hydrogen, in each case optionally substituted alkyl, alkenyl, alkinyl, alkoxycarbonyl, alkenoxycarbonyl, alkinoxycarbonyl or alkylcarbonyl or where the radicals $R^2$ and $R^3$, together with the nitrogen atom enclosed by them, form a ring,
$R^4$ represents hydrogen, phenyl or optionally substituted alkyl,
Ar represents, in each case optionally substituted, phenyl or naphthyl,
$Y^1$ represents halogen and
$Y^2$ represents optionally substituted alkyl or halogen.

Furthermore it has been found that the substituted 2-arylpyrroles of the general formula (I), in which $R^1$, $R^2$, $R^3$, $R^4$, Ar, $Y^1$ and $Y^2$ have the abovementioned meaning, are obtained
if 2-arylpyrroles of the formula (II)

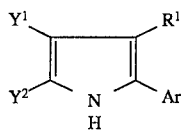

in which
$R^1$, Ar, $Y^1$ and $Y^2$ have the abovementioned meaning, are reacted with compounds of the formula (III)

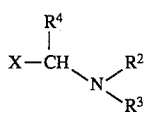

in which
$R^2$, $R^3$ and $R^4$ have the abovementioned meaning and
X represents an anionic leaving group,
optionally in the presence of bases and/or optionally in the presence of diluents.

Finally it was found that novel substituted 2-arylpyrroles of the formula (I) possess strongly pronounced biological properties and are suitable in particular for combating animal pests, in particular insects, arachnids and nematodes, encountered in agriculture, in forestry, in the protection of stored products and of materials, and in the hygiene field.

The novel substituted 2-arylpyrroles according to the invention are defined by the general formula (I).

2-Arylpyrroles of the above formula (I) are preferred in which
$R^1$ represents cyano or nitro,
$R^2$ and $R^3$, independently of each other, either represent hydrogen, $C_1$–$C_8$-alkyl, $C_3$–$C_8$-alkenyl or $C_3$–$C_8$-alkinyl, where the alkyl, alkenyl or alkinyl radicals are optionally substituted by 1 to 6 identical or different halogen atoms, $C_1$–$C_6$-alkoxy, $C_1$–$C_6$-alkylthio, ($C_1$–$C_6$-alkyl)carbonyloxy, ($C_1$–$C_6$-alkoxy)-carbonyl, optionally substituted phenyl, cyano or nitro, or represent ($C_1$–$C_8$-alkoxy)-carbonyl, ($C_3$–$C_8$-alkenoxy)-carbonyl or ($C_3$–$C_8$-alkinoxy)-carbonyl, where the alkoxy, alkenoxy or alkinoxy moiety is in each case optionally substituted by 1 to 6 identical or different radicals from the series halogen, $C_1$–$C_6$-alkoxy, $C_1$–$C_6$-alkylthio, ($C_1$–$C_6$-alkyl)carbonyloxy, ($C_1$–$C_6$-alkoxy)-carbonyl, optionally substituted phenyl, cyano or nitro, or represent ($C_1$–$C_8$-alkyl)carbonyl, which is optionally substituted by 1–6 identical or different radicals from the series halogen, $C_1$–$C_6$-alkoxy, $C_1$–$C_6$-alkylthio, ($C_1$–$C_6$-alkyl)carbonyloxy, ($C_1$–$C_6$-alkoxy)-carbonyl, optionally substituted phenyl, cyano or nitro, or $R^2$ and $R^3$, together with the nitrogen enclosed by them, form a 4- to 8-membered ring,
$R^4$ represents hydrogen, phenyl or $C_1$- to $C_8$-alkyl, which is optionally substituted by 1 to 6 radicals from the series halogen, $C_1$–$C_6$-alkoxy, $C_1$–$C_6$-alkylthio, ($C_1$–$C_6$-alkyl)carbonyloxy, ($C_1$–$C_6$-alkoxy)-carbonyl, phenyl, cyano or nitro,
Ar represents phenyl, which is optionally substituted identically or differently once to five times by halogen, $C_1$–$C_8$-alkyl, $C_2$–$C_8$-alkenyl or $C_2$–$C_8$-alkinyl, where the alkyl, alkenyl or alkinyl radicals are optionally substituted by 1 to 6 radicals from the series halogen, $C_1$–$C_5$-alkoxy, which is optionally substituted by 1 to 6 halogen atoms, or $C_1$–$C_5$-alkylthio, which is optionally substituted by 1 to 6 radicals from the series halogen or ($C_1$–$C_5$-alkyl)carbonyloxy, by $C_1$–$C_8$-alkoxy, $C_2$–$C_8$-alkenoxy or $C_2$–$C_8$-alkinoxy, where the alkoxy, alkenoxy or alkinoxy radicals are optionally substituted by 1 to 6 halogen atoms, by $C_1$–$C_8$-alkylthio, $C_2$–$C_8$-alkenylthio or $C_2$–$C_8$-alkinylthio, where the alkylthio, -alkenylthio or alkinylthio radicals are optionally substituted by 1 to 6 halogen atoms, by ($C_1$–$C_8$-alkyl)carbonyloxy, which is optionally substituted by 1 to 6 halogen atoms, by amino, which is optionally substituted by 1 to 2 identical or different alkyl radicals with 1 to 8 carbon atoms, which are optionally substituted by 1 to 6 halogen atoms, by nitro or cyano,
$Y^1$ represents halogen and
$Y^2$ represents halogen or $C_1$–$C_6$-alkyl, which is optionally substituted identically or differently by 1 to 8 halogen atoms.

Substituted 2-arylpyrroles of the general formula (I) are particularly preferred in which
$R^1$ represents cyano or nitro,
$R^2$ and $R^3$, independently of each other, either represent hydrogen, $C_1$–$C_6$-alkyl, $C_3$–$C_6$-alkenyl or $C_3$–$C_6$-alkinyl, where the alkyl, alkenyl or alkinyl radicals are optionally substituted by 1 to 5 radicals from the series fluorine and/or chlorine, $C_1$–$C_4$-alkoxy, $C_1$–$C_4$-alkylthio, $C_1$–$C_4$-acyloxy, ($C_1$–$C_4$-alkoxy)-carbonyl, optionally substituted phenyl, cyano or nitro, or represent ($C_1$–$C_6$-alkoxy)-carbonyl, ($C_3$–$C_6$-alkenoxy)-carbonyl or ($C_3$–$C_6$-alkinoxy)-carbonyl, where the alkoxy, alkenoxy or alkinoxy moiety is optionally substituted by 1 to 5 radicals from the series fluorine and/or chlorine, $C_1$–$C_4$-alkoxy, $C_1$–$C_4$-alkylthio, $C_1$–$C_4$-acyloxy, ($C_1$–$C_4$-alkoxy)-carbonyl, optionally substituted phenyl, cyano or nitro, or represent ($C_1$–$C_6$-alkyl)carbonyl, which is optionally substituted by 1 to 5 radicals from the series fluorine and/or chlorine, ($C_1$–$C_4$-alkoxy)-carbonyl, optionally substituted phenyl, cyano or nitro, or $R^2$ and $R^3$, together with the nitrogen atom enclosed by them, form a 4- to 6-membered ring, $R^4$ represents hydrogen, phenyl or $C_1$- to $C_6$-alkyl, which is optionally substituted by 1 to 5 radicals from the series fluorine and/or chlorine, $C_1$–$C_4$-alkoxy, $C_1$–$C_4$-alkylthio, $C_1$–$C_4$-acyloxy, ($C_1$–$C_4$-alkoxy)-carbonyl, phenyl, cyano or nitro, Ar represents phenyl, which is optionally substituted identically or differently once to four times by fluorine, chlorine or bromine, $C_1$–$C_6$-alkyl, $C_2$–$C_6$-alkenyl or $C_2$–$C_6$-alkinyl, where the alkyl, alkenyl or alkinyl radicals are optionally substituted by 1 to 5 fluorine and/or chlorine atoms, $C_1$–$C_4$-alkoxy, which is optionally substituted by 1 to 5 fluorine and/or chlorine atoms, or $C_1$–$C_4$-alkylthio, which is optionally substituted by 1 to 5 fluorine and/or chlorine atoms or $C_1$–$C_4$-acyloxy, by $C_1$–$C_6$-alkoxy, $C_2$–$C_6$-alkenoxy or $C_2$–$C_6$-alkinoxy, where the alkoxy, alkenoxy or alkinoxy radicals are optionally substituted by 1 to 5 fluorine and/or chlorine atoms, by $C_1$–$C_6$-alkylthio, $C_2$–$C_6$-alkenylthio or alkinylthio, where the alkylthio, alkenylthio or alkinylthio radicals are optionally substituted by 1 to 5 fluorine and/or chlorine atoms, by ($C_1$–$C_6$-alkyl)carbonyloxy, which is optionally substituted by 1 to 5 fluorine and/or chlorine atoms, by amino, which is optionally substituted by 1 to 2 identical or different alkyl radicals with 1 to 6 carbon atoms, which are optionally substituted by 1 to 5 fluorine and/or chlorine atoms, by nitro or cyano, $Y^1$ represents chlorine or bromine and $Y^2$ represents chlorine or bromine or $C_1$–$C_5$-alkyl, which is optionally substituted identically or differently by 1 to 7 fluorine and/or chlorine atoms.

If 4-bromo-3-cyano-2-(4-chlorophenyl)-5-trifluoromethylpyrrole and ethyl N-methyl-N-chloromethyl-carbamate are used as starting compounds according to the given process, the course of the reaction can be represented by the following reaction diagram:

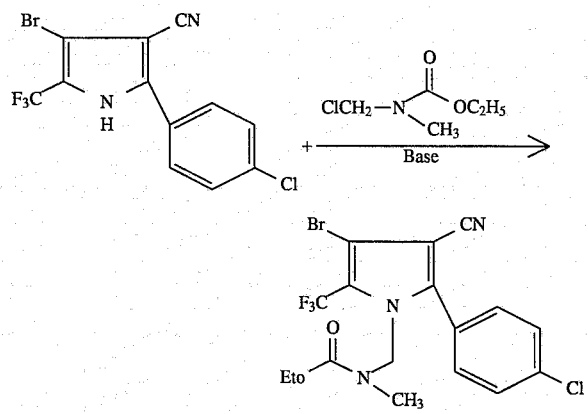

If 2-(4-chlorophenyl)-3-cyano-4,5-dichloropyrrole and N-chloromethylpyrrolidine are used as starting compounds according to the given process, the course of the reaction can be represented by the following reaction diagram:

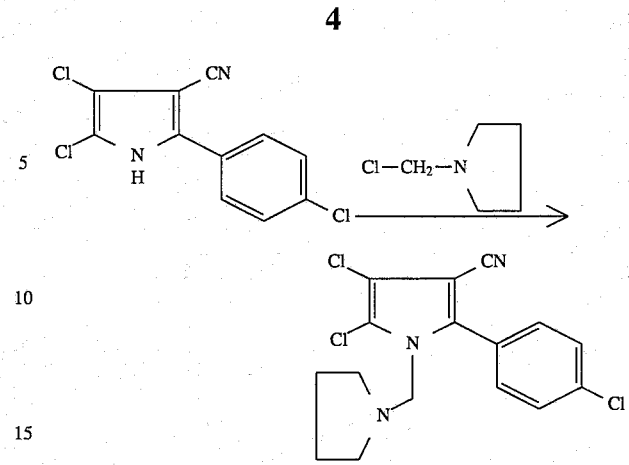

The starting compounds of the general formula (II) used in the preparation process are known and can be prepared by known methods (see e.g. I. A. Benages et al, J. Org. Chem. 43, 4278 (1978), EP-A 0 347 480, EP-O 426 948 A1 or U.S. Pat. No. 5,030,735).

The starting compounds of the general formula (III) which are used in the preparation process are also known or can be prepared by methods which are known in principle (see e.g. K. G. Siver et al, J. Pharm. Sci. 79, 66 (1990)).

The process for preparing compounds of the formula (I) is characterised in that compounds of the formula (II) are reacted with compounds of the formula (III), optionally in the presence of bases and optionally in the presence of diluents.

All inert organic solvents are suitable diluents. These preferably include hydrocarbons, such as benzene, toluene or xylene, as well as ethers, such as dibutyl ether, tert-butyl methyl ether, tetrahydrofuran or dioxane, and polar solvents, such as dimethyl sulphoxide, acetonitrile, sulpholane, dimethylformamide and N-methylpyrrolidone.

All customary proton acceptors may be employed as bases. Those which are preferably employed are oxides, hydroxides and carbonates of alkali metals and alkaline earth metals, such as sodium hydroxide, potassium hydroxide, magnesium oxide, calcium oxide, sodium carbonate, potassium carbonate and calcium carbonate, which may also be employed in the presence of phase transfer catalysts, such as, for example, triethylbenzylammonium chloride, tetrabutylammonium bromide and 18-crown-6. Furthermore, amides and hydrides of alkali metals and alkaline earth metals, such as sodium amide, sodium hydride and calcium hydride, as well as alkali metal alcoholates, such as sodium methylate, sodium ethylate and potassium tert-butylate, may be employed.

In carrying out the process, the reaction temperatures may be varied over quite a wide range. In general, temperatures between –10° C. and 200° C., preferably between 0° C. and 120° C., are employed.

In carrying out the process, the reaction components of the formulae (II), the deprotonating bases and the components of the formulae (III) are generally employed in approximately equimolar quantities. However, it is also possible to use one or another component in a relatively large excess (up to 3 mol).

The process is generally carried out under atmospheric pressure, but can also be carried out under elevated pressure.

The substituted 2-arylpyrroles (I) according to the invention are suitable for combating animal pests, in particular insects, arachnids and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*.

From the order of the Chilopoda, for example, *Geophilus carpophagus* and *Scutigera spec*. From the order of the Symphyla, for example, *Scutigerella immaculata*.

From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria*.

From the order of the Dermaptera, for example, *Forficula auricularia*.

From the order of the Isoptera, for example, *Reticulitermes spp.*. From the order of the Anoplura, for example, *Phylloxera vastatrix, Pemphigus spp., Pediculus humanus corporis, Haematopinus spp.* and *Linognathus spp*. From the order of the Mallophaga, for example, *Trichodectes spp.* and *Damalinea spp.*

From the order of the Thysanoptera, for example, *Hercinothrips femoralis* and *Thrips tabaci*. From the order of the Heteroptera, for example, *Eurygaster spp., Dysdercus intermedius, Piesma quadrata, Cimex lectularius, Rhodnius prolixus* and *Triatoma spp.* From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.* From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*.

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*.

From the order of the Siphonaptera, for example, *Xenopsylla cheopis* and *Ceratophyllus spp.* From the order of the Arachnida, for example, *Scorpio maurus, Latrodectus mactans*.

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp.*.

The substituted 2-arylpyrroles (I) according to the invention are not only active against plant, hygiene and stored product pests, but also, in the veterinary medicine sector, against animal parasites (ectoparasites), such as scaly ticks, argasidae, scab mites, trombidae, flies (stinging and sucking), parasitic fly larvae, lice, hair lice, bird lice and fleas. They are active against normally sensitive and resistant species and strains, as well as against all parasitic and non-parasitic stages of development of the ectoparasites.

The substituted 2-arylpyrroles (I) according to the invention have a strong insecticidal action. They can be employed particularly successfully against insects which are harmful to plants, such as, for example, against the larvae of the mustard beetle (*Phaedon cochleariae*), against the green peach aphid (*Myzus persicae*) or against the black bean aphid (*Aphis fabae*). In this context the active compounds according to the invention show not only protective properties but also systemic properties in the leaves and roots.

In addition, the substituted 2-arylpyrroles (I) according to the invention are also extremely suitable for combating soil insects and can be employed in the soil, for example, for combating grubs of the onion fly (*Phorbia antiqua*).

In addition, the substituted 2-arylpyrroles (I) according to the invention according to the invention have a high activity against hygiene pests and stored product pests and can be employed, for example, for combating cockroaches (*Blatella germanica*).

The substituted 2-arylpyrroles (I) according to the invention can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the substituted 2-arylpyrroles (I) according to the invention with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl iosbutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The substituted 2-arylpyrroles (I) according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The substituted 2-arylpyrroles (I) according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The substituted 2-arylpyrroles (I) according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The application of the substituted 2-arylpyrroles (I) according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as moulded articles (collar, ear tag) is also possible.

The biological effectiveness of the compounds according to the invention will be explained with reference to the application examples.

PREPARATION EXAMPLES

Example 1

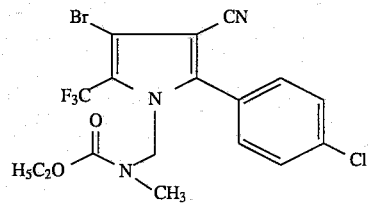

3 g (8.6 mmol) of 4-bromo-3-cyano-2-(4-chlorophenyl)-5-trifluoromethyl-pyrrole are dissolved in 50 ml of dry THF, and 1.06 g (9.4 mmol) of potassium tert-butylate are added. 1.34 g (9 mmol) of ethyl N-methyl-N-chloromethylcarbamate, dissolved in 10 ml of dry THF, are next added and the mixture is stirred at room temperature for 16 h.

The mixture is poured onto water and extracted with $CH_2Cl_2$. The org. phases are combined and dried over $Na_2SO_4$. After rotary evaporation, purification is carried out by chromatography on silica gel ($CH_2Cl_2$). Yield 2.9 g (73% of theory) of the compound of the above formula (physical data: see Table 1).

In an analogous manner, and taking account of the details in the description, the substances of the formula (I) which are listed below in Table 1 are obtained.

TABLE 1

| Preparation example No. | R¹ | R² | R³ | R⁴ | Y¹ | Y² | Ar | Phys. data |
|---|---|---|---|---|---|---|---|---|
| 1 | CN | −C(=O)OC₂H₅ | H | H | Br | −CF₃ | 4-Cl-C₆H₄- | ¹H-NMR(CDCl₃)δ=1.15(t, 3H), 2.51 (s, 3H), 3.92(q, 2H), 5.60(s, 2H)7.31 (d, 2H), 7.51(d, 2H) |
| 2 | CN | −C₂H₅ | H | H | Br | −CF₃ | " | |
| 3 | −CN | −CH₂CH₂CH(CH₃)₂ | −C(=O)−OC₅H₁₁ | H | Br | −CF₃ | " | |
| 4 | −CN | −C(CH₃)₃ | −C(=O)−OCH₂CH(CH₃)₂ | | | −CF₃ | " | |
| 5 | −CN | −CH₂CH(CH₃)₂ | −C(=O)−OCH₃ | H | Br | −CF₃ | " | |
| 6 | −CN | −C₄H₉ | −C(=O)O−C₃H₇ | H | Cl | Cl | 4-Cl-C₆H₄- | |
| 7 | −CN | −C₃H₇ | −C(=O)O−CH₃ | −CH₃ | Cl | Cl | " | |
| 8 | −NO₂ | −C₂H₅ | −C(=O)O−C₂H₅ | −H | Br | Br | " | |
| 9 | −CN | −CH₃ | −C(=O)O−C₄H₉ | −H | Cl | Cl | " | |
| 10 | −CN | −CH₃ | −C(=O)OC₂H₅ | −H | Br | Br | 2-OCF₃-5-CH₃-C₆H₃- (OCF₃) | ¹H-NMR(CDCl₃)δ=1.15(3H, t), 2.52 (3H, s), 3.95(2H, q), 5.55(2H, s), 7.30 (2H, d), 7.50(2H, d) |
| 11 | −CN | −CH₃ | −COC₂H₅ (O=) | H | Br | Br | " | ¹H-NMR(CDCl₃)δ=1.13(3H, t), 2.60 (3H, s), 3.92(2H, q), 5.59(2H, s)7.25–7.60(3H, m) |

TABLE 1-continued

| Preparation example No. | R¹ | R² | R³ | R⁴ | Y¹ | Y² | Ar | Phys. data |
|---|---|---|---|---|---|---|---|---|
| 12 | —CN | —C₄H₉ | —C(=O)—OC₃H₇ | CH₃ | Br | Br | " | |
| 13 | —CN | —C₆H₁₃ | —C(=O)—OCH₂CH(CH₃)₂ | H | Br | Br | 2-OCF₃, 1-OCF₃ phenyl | |
| 14 | —CN | —C₂H₅ | —C(=O)—OCH(C₂H₅)(CH₃) | H | Cl | Cl | 2,3-diCl phenyl | ¹H-NMR(CDCl₃)δ=0.85(t, 3H), 1.18 (t, 3H), 2.90(q, 2H)3.95(q, 2H), 5.60 (s, 2H), 7.20(d, 1H)7.45(d, 1H), 7.60(d, 1H) |
| 15 | —CN | —C₂H₅ | —C(=O)—OC₂H₅ | H | Br | CF₃ | " |  |
| 16 | —CN | —CH₃ | —C(=O)—OC₂H₅ | H | Cl | Cl | 3-Cl phenyl |  |
| 17 | —CN | —C₃H₇ | —C(=O)—OC₄H₉ | H | Br | Br | 2,4,6-triCl phenyl |  |
| 18 | —CN | —C₃H₇ | —C₃H₇ | H | Br | Br | 2,5-diCl phenyl |  |
| 19 | —CN | —C₃H₇ | —CH₂CH=CH₂ | H | Br | —CF₃ | 4-F phenyl |  |

TABLE 1-continued
| Preparation example No. | R¹ | R² | R³ | R⁴ | Y¹ | Y² | Ar | Phys. data |
|---|---|---|---|---|---|---|---|---|
| 20 | —CN | CH₃ | 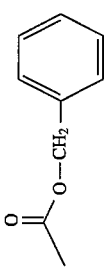 | H | Br | —CF₃ | 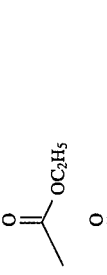 3-F | |
| 21 | —CN | —CH₂CH=CH₂ | —C(O)OC₂H₅ | H | Br | —CF₃ |  2-F | |
| 22 | —CN | —C(O)OC₂H₅ | —C(O)OC₂H₅ | H | Br | —CF₃ | " | |
| 23 | —CN | —CH₂CF₃ | —C(O)OC₂H₅ | H | Br | Br |  4-CF₃ | |
| 24 | —CN | —C(O)OCH₃ | —C(O)OCH₃ | H | Cl | Cl |  4-OC₂H₅ | |
| 25 | —CN | —C₅H₁₁ | —C(O)OC₂H₅ | H | Cl | Cl |  4-CH₃ | |
| 26 | —CN | CH₃ | —C(O)OC₃H₇ | H | Br | Br |  3,5-Cl₂ | |
| 27 | —CN | —C₂H₅ | —C(O)OC₂H₅ | H | Br | Br |  4-OCF₃ | |

TABLE 1-continued
| Preparation example No. | R¹ | R² | R³ | R⁴ | Y¹ | Y² | Ar | Phys. data |
|---|---|---|---|---|---|---|---|---|
| 28 | —CN | —C₂H₅ | —C₂H₅ | H | Br | CF₃ |  | |
| 29 | —CN | —(CH₂)₅— | | H | Br | CF₃ |  | |
| 30 | —CN | —CH₂—CH₂—CH₂—CH₂— | | H | Br | Br |  | |
| 31 | —CN | —C₄H₉ | —C₄H₉ | H | Br | —CF₃ |  | Mp = 120° C. |
| 32 | —CN | —CH₃ |  | H | Br | —CF₃ |  | |
| 33 | —CN | —C₄H₉ |  | H | Br | —CF₃ |  | |
| 34 | —CN | —C₂H₅ |  | H | Br | —CF₃ |  | ¹H-NMR(CDCl₃)δ=1.15(t, 3H), 2.50 (s, 3H), 3.95(q, 2H), 5.60(s, 2H), 7.20–7.40(m, 4H) |
| 35 | —CN | —CH₂CH(CH₃)₂ |  | H | Br | —CF₃ |  | Mp = 114° C. |

TABLE 1-continued

| Preparation example No. | R¹ | R² | R³ | R⁴ | Y¹ | Y² | Ar | Phys. data |
|---|---|---|---|---|---|---|---|---|
| 36 | —CN | cyclohexyl-H | —C(O)O—CH₃ | H | Br | —CF₃ | 4-F-C₆H₄ | Mp = 110° C. |
| 37 | —CN | —C₂H₅ | —C(O)O—CH₃ | H | Br | —CF₃ | " | |
| 38 | —CN | —CH₃ | —C(O)OC₂H₅ | H | Br | —CF₃ | 2-F-C₆H₄ | |
| 39 | —CN | —C₃H₇ | —C(O)OC₂H₅ | H | Br | —CF₃ | 2-F-C₆H₄ | ¹H-NMR(CDCl₃)δ=0.70(t, 3H), 1.15(t, 3H), 1.20(m, 2H), 2.80 (q, 2H), 3.90(q, 2H), 5.65 (s, 2H), 7.2–7.6(m, 4H) |
| 40 | —CN | | —CH₂—CH₂—C(O)CH₂— | H | Br | —CF₃ | 2-F-C₆H₄ | |
| 41 | —CN | —C₂H₅ | —C(O)OC₂H₅ | H | Br | —CF₂CF₂ | 2,4-Cl₂-C₆H₃ | |
| 42 | —CN | —CH₃ | —C(O)OC₂H₅ | H | Br | —CF₂CF₂CF₃ | 2,4-Cl₂-C₆H₃ | |

TABLE 1-continued
| Preparation example No. | $R^1$ | $R^2$ | $R^3$ | $R^4$ | $Y^1$ | $Y^2$ | Ar | Phys. data |
|---|---|---|---|---|---|---|---|---|
| 43 | —CN | —CH$_3$ | 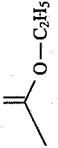 | H | Br | —CF$_3$ |  | Mp = 90° C. |
| 44 | —CN | —C$_2$H$_5$ |  | H | Br | —CF$_3$ |  | |
| 45 | —CN | —C$_2$H$_5$ |  | H | Br | —CH$_3$ |  | |
| 46 | —CN | —CH$_3$ | 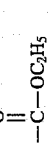 | H | Br | —CF$_3$ |  | $^1$H-NMR(CDCl$_3$)δ=1.15(3H, t), 2.50(3H, s), 3.95(2H, q), 4.55(2H, s), 5.60(2H, s), 7.20–7.50(4H, m) |
| 47 | —CN | —CH$_2$CH(CH$_3$)$_2$ |  | H | Br | —CF$_3$ |  | IR (Film) = 2280, 1705, 1180 cm$^{-1}$ |
| 48 | —CN | —CH$_3$ |  | H | Br | —CF$_3$ |  | |
| 49 | —CN | —CH$_3$ |  | H | Br | —CF$_3$ |  | Mp = 122° C. |
| 50 | —CN | —CH$_3$ |  | H | Br | Br |  | Mp = 112° C. |

TABLE 1-continued
| Preparation example No. | R$^1$ | R$^2$ | R$^3$ | R$^4$ | Y$^1$ | Y$^2$ | Ar | Phys. data |
|---|---|---|---|---|---|---|---|---|
| 51 | —CN | —C$_2$H$_5$ | —C(=O)—OC$_2$H$_5$ | H | Br | —CF$_3$ |  | $^1$H-NMR(CDCl$_3$)δ=0.80(t, 3H), 1.15(t, 3H), 2.95(q, 2H), 5.60(s, 2H), 7.2–7.7(m, 4H) |
| 52 | —CN | —C$_3$H$_7$ | —C(=O)—OC$_2$H$_5$ | H | Br | —CF$_3$ |  | $^1$H-NMR(CDCl$_3$)δ=0.75(t, 3H), 1.1–1.3(m, 2H), 2.80(dd, 2H), 3.8 (q, 2H), 5.60(s, 2H), 7.20(d, 1H), 7.45 (d, 1H), 7.60(d, 1H) |
| 53 | —CN | —CH$_2$CH(CH$_3$)$_2$ | —C(=O)—OCH$_3$ | H | Br | —CF$_3$ |  | $^1$H-NMR(CDCl$_3$)δ=0.75(d, 6H), 1.5(m, 1H), 2.65(d, 2H), 3.50(s, 3H), 5.60(s, 2H), 7.2–7.6(m, 3H) |

APPLICATION EXAMPLES

In the following application examples the following compound was employed as the comparison substance:

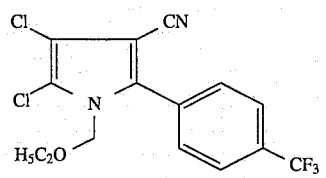 (A)

1-(Ethoxymethyl)-2-(4-trifluoromethyl-phenyl)-3-cyano-4,5-dichloro-pyrrole known from EP-A 0 347 488

Example A

Tetranychus test (OP-resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentrations.

Bean plants (*Phaseolus vulgaris*) which are heavily infested with all the developmental stages of the two-spotted spider mite (*Tetranychus urticae*) are dipped into a preparation of the active compound of the desired concentration.

After the desired period of time, the effect in % is determined. 100% means that all the spider mites have been killed; 0% means that none of the spider mites has been killed.

In this test, the following compound, for example, of the preparation examples shows superior efficacy as compared with the state of the art: (1), (43), (49).

TABLE A (Plant-damaging mites)
Tetranychus test (OP-resistant)

| Active compound | Concentration of active compound in % | Degree of destruction in % after 7 days |
|---|---|---|
| Compound known from EP-A 347 488; [structure with Cl, Cl, CN, H₅C₂O, CF₃] | 0.0001 | 0 |
| Compound known from EP-A 347 488; [structure with Br, F₃C, CN, H₅C₂O, Cl] | 0.0001 | 80 |

TABLE A-continued (Plant-damaging mites)
Tetranychus test (OP-resistant)

| Active compound | Concentration of active compound in % | Degree of destruction in % after 7 days |
|---|---|---|
| Compounds according to the invention | | |
| [structure (43): Br, F₃C, OC₂H₅, CN, CH₃, Cl, Cl] | 0.0001 | 98 |
| [structure (49): Br, F₃C, OCH₃, CN, CH₃, Cl, Cl] | 0.0001 | 98 |

Example B

Fly test

Solvent: 35 parts by weight of ethyleneglycol monomethyl ether

Emulsifier: 35 parts by weight of nonylphenol polyglycol ether

In order to prepare a suitable formulation, 3 parts by weight of active compound are mixed with seven parts of the abovementioned solvent-emulsifier mixture, and the emulsion concentrate thus obtained is diluted with water to the concentration which is desired on each occasion.

2 ml of this preparation of the active compound are pipetted onto filter paper discs (φ 9.5 cm) which are located in Petri dishes of corresponding size. After drying the filter discs, 25 test animals are transferred into the Petri dishes and covered over.

After 6 hours, the efficacy of the preparation of the active compound is determined. The efficacy is expressed in %. 100% means that all the flies have been killed; 0% means that none of the flies has been killed.

In this test, the following compounds according to the invention, for example, showed outstanding biological efficacy: compounds from preparation examples (15), (36).

TABLE B

Fly test/*Musca domestica*, strain WHO (N)

| Active compound | Concentration of active compound in ppm of active ingredient | Destructive effect on *Musca domestica* in % |
|---|---|---|
| Compound (15): pyrrole with Br, CN, F₃C, N-CH₂-N(C₂H₅)-C(=O)-OC₂H₅, and 3,4-dichlorophenyl substituents | 1000 | 100 |
| Compound (36): pyrrole with Br, CN, F₃C, N-CH₂-N(cyclohexyl)-C(=O)-OCH₃, and 4-fluorophenyl substituents | 1000 | 100 |

Example C

Cockroach test

Test animals: *Blattella germanica*

Solvent: 35 parts by weight of ethyleneglycol monomethyl ether

Emulsifier: 35 parts by weight of nonylphenol polyglycol ether

In order to prepare a suitable formulation, 3 parts by weight of active compound are mixed with seven parts of the abovementioned solvent-emulsifier mixture and the emulsion concentrate thus obtained is diluted with water to the concentration which is desired on each occasion.

2 ml of this preparation of the active compound are pipetted onto filter paper discs (φ 9.5 cm) which are located in Petri dishes of the corresponding size. After drying the filter discs, 5 test animals are transferred to the Petri dishes and covered over.

After 3 days, the efficacy of the preparation of the active compound is determined. The efficacy is expressed in %. 100% means that all the cockroaches have been killed; 0% means that none of the cockroaches has been killed.

In this test, the following compounds according to the invention, for example, showed outstanding biological efficacy: compounds from preparation examples (1), (15), (36), (52).

TABLE C

Cockroach test/*Blatella germanica*

| Active compound | Concentration of active compound in ppm of active ingredient | Destructive effect on *Blatella germanica* in % |
|---|---|---|
| Compound (15): pyrrole with Br, CN, F₃C, N-CH₂-N(C₂H₅)-C(=O)-OC₂H₅, and 3,4-dichlorophenyl substituents | 1000 | 100 |
| | 300 | 100 |
| | 100 | 100 |
| Compound (36): pyrrole with Br, CN, F₃C, N-CH₂-N(cyclohexyl)-C(=O)-OCH₃, and 4-fluorophenyl substituents | 1000 | 100 |
| Compound (52): pyrrole with Br, CN, F₃C, N-CH₂-N(C₃H₇)-C(=O)-OC₂H₅, and 3,4-dichlorophenyl substituents | 1000 | 100 |

Example D

Blowfly larvae test

Test animals: *Lucilia cuprina* larvae

Solvent: 35 parts by weight of ethyleneglycol mono methyl ether

Emulsifier: 35 parts by weight of nonylphenol polyglycol ether

To prepare an expedient preparation of the active compound, 3 parts by weight of active compound are mixed with 7 parts by weight of the abovementioned mixture, and the emulsion concentrate thus obtained is diluted with water to the concentration which is required on each occasion.

About 20 *Lucilia cuprina* res. larvae are placed in a test tube, which contains about 1 cm³ of horse meat and 0.5 ml of the preparation of the active compound. After 24 hours, the efficacy of the preparation of the active compound is determined. 100% means that all the blowfly larvae have been killed; 0% means that none of the blowfly larvae has been killed.

In this test, the following compounds, for example, showed an outstanding biological efficacy: compounds from preparation examples: (15), (52).

TABLE D

Blowfly larvae test
*Lucilia cuprina* larvae

| Compound | Concentration of active compound in ppm of active ingredient | Destructive effect on *Lucilia cuprina* larvae in % |
|---|---|---|
| (15) Br, CN, F₃C, N, H₅C₂—N, O, OC₂H₅, Cl, Cl | 1000 | 100 |
| (52) Br, CN, F₃C, N, H₇C₃—N, O, OC₂H₅, Cl, Cl | 1000 | 100 |

Example E

Plutella test

Solvent: 7 parts by weight of dimethylformamide
Emulsifier: 1 part by weight of alkylaryl polyglycol ether To produce an expedient preparation of active compound, 1 part by weight of active compound is mixed with the stated amount of solvent and the stated amount of emulsifier, and the concentrate is diluted with water to the desired concentrations.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars has been killed.

In this test, the following compounds, for example, of the preparation examples show superior efficacy as compared with the state of the art: (1).

What is claimed is:

1. Substituted 2-arylpyrroles of the general formula (I)

$$\begin{array}{c} Y^1 \diagdown \diagup R^1 \\ Y^2 \diagdown N \diagup Ar \\ | \\ R^2 - N \diagdown R^4 \\ | \\ R^3 \end{array} \quad (I)$$

in which

R¹ represents cyano or nitro,

R² and R³, independently of each other, represent hydrogen, in each case optionally substituted alkyl, alkenyl, alkinyl, alkoxycarbonyl, alkenoxycarbonyl, alkinoxycarbonyl or where the radicals R² and R³, together with the nitrogen atom enclosed by them, form a ring, R⁴ represents hydrogen, phenyl or optionally substituted alkyl, Ar represents, in each case optionally substituted, phenyl or naphthyl, Y¹ represents halogen and Y² represents optionally substituted alkyl or halogen.

2. 2-Arylpyrroles of the formula (I) according to claim 1, in which

R¹ represents cyano or nitro,

R² and R³, independently of each other, either represent hydrogen, $C_1$–$C_8$-alkyl, $C_3$–$C_8$-alkenyl or $C_3$–$C_8$-alkinyl, where the alkyl, alkenyl or alkinyl radicals are optionally substituted by 1 to 6 identical or different halogen atoms, $C_1$–$C_6$-alkoxy, $C_1$–$C_6$-alkylthio, ($C_1$–$C_6$-alkyl)carbonyloxy, ($C_1$–$C_6$-alkoxy)-carbonyl, optionally substituted phenyl, cyano or nitro, or represent ($C_1$–$C_8$-alkoxy)-carbonyl, ($C_3$–$C_8$-alkenoxy)-carbonyl or ($C_3$–$C_8$-alkinoxy)-carbonyl, where the alkoxy, alkenoxy or alkinoxy moiety is in each case optionally substituted by 1 to 6 identical or different radicals from the series halogen, $C_1$–$C_6$-alkoxy, $C_1$–$C_6$-alkylthio, ($C_1$–$C_6$-alkyl)carbonyloxy, ($C_1$–$C_6$-alkoxy)-carbonyl, optionally substituted phenyl, cyano or nitro, or R² and R³, together with the nitrogen enclosed by them, form a 4- to 8-membered ring, R⁴ represents hydrogen, phenyl or $C_1$- to $C_8$-alkyl, which is optionally substituted by 1 to 6 radicals from the series halogen, $C_1$–$C_6$-alkoxy, $C_1$–$C_6$-alkylthio, ($C_1$–$C_6$-alkyl)carbonyloxy, ($C_1$–$C_6$-alkoxy)-carbonyl, phenyl, cyano or nitro, Ar represents phenyl, which is optionally substituted identically or differently once to five times by halogen, $C_1$–$C_8$-alkyl, $C_2$–$C_8$-alkenyl or $C_2$–$C_8$-alkinyl, where the alkyl, alkenyl or alkinyl radicals are optionally substituted by 1 to 6 radicals from the series halogen, $C_1$–$C_5$-alkoxy, which is optionally substituted by 1 to 6 halogen atoms, or $C_1$–$C_5$-alkylthio, which is optionally substituted by 1 to 6 radicals from the series halogen or ($C_1$–$C_5$-alkyl)-carbonyloxy, by $C_1$–$C_8$-alkoxy, $C_2$–$C_8$-alkenoxy or $C_2$–$C_8$-alkinoxy, where the alkoxy, alkenoxy or alkinoxy radicals are optionally substituted by 1 to 6 halogen atoms, by $C_1$–$C_8$-alkylthio, $C_2$–$C_8$-alkenylthio or $C_2$–$C_8$-alkinylthio, where the alkylthio, -alkenylthio or alkinylthio radicals are optionally substituted by 1 to 6 halogen atoms, by ($C_1$–$C_8$-alkyl)carbonyloxy, which is optionally substituted by 1 to 6 halogen atoms, by amino, which is optionally substituted by 1 to 2 identical or different alkyl radicals with 1 to 8 carbon atoms, which are optionally substituted by 1 to 6 halogen atoms, by nitro or cyano, Y¹ represents halogen and Y² represents halogen or $C_1$–$C_6$-alkyl, which is optionally substituted identically or differently by 1 to 8 halogen atoms.

3. 2-Arylpyrroles of the general formula (1) according to claim 1, in which

R¹ represents cyano or nitro,

R² and R³, independently of each other, either represent hydrogen, $C_1$–$C_6$-alkyl, $C_3$–$C_6$-alkenyl or $C_3$–$C_6$-alkinyl, where the alkyl, alkenyl or alkinyl radicals are optionally substituted by 1 to 5 radicals from the series fluorine and/or chlorine, $C_1$–$C_4$-alkoxy, $C_1$–$C_4$-alkylthio, $C_1$–$C_4$-acyloxy, ($C_1$–$C_4$-alkoxy)-carbonyl, optionally substituted phenyl, cyano or nitro, or represent $(C_1-C_6\text{-alkoxy})$-carbonyl, $(C_3-C_6\text{-alkenoxy})$-carbonyl or $(C_3-C_6\text{-alkinoxy})$-carbonyl, where the alkoxy, alkenoxy or alkinoxy moiety is optionally substituted by 1 to 5 radicals from the series fluorine and/or chlorine, $C_1-C_4$-alkoxy, $C_1-C_4$-alkylthio, $C_1-C_4$-acyloxy, $(C_1-C_4\text{-alkoxy})$-carbonyl, optionally substituted phenyl, cyano or nitro, or $R^2$ and $R^3$, together with the nitrogen atom enclosed by them, form a 4- to 6-membered ring, $R^4$ represents hydrogen, phenyl or $C_1$- to $C_6$-alkyl, which is optionally substituted by 1 to 5 radicals from the series fluorine and/or chlorine, $C_1-C_4$-alkoxy, $C_1-C_4$-alkylthio, $C_1-C_4$-acyloxy, $(C_1-C_4\text{-alkoxy})$-carbonyl, phenyl, cyano or nitro, Ar represents phenyl, which is optionally substituted identically or differently once to four times by fluorine, chlorine or bromine, $C_1-C_6$-alkyl, $C_2-C_6$-alkenyl or $C_2-C_6$-alkinyl, where the alkyl, alkenyl or alkinyl radicals are optionally substituted by 1 to 5 fluorine and/or chlorine atoms, $C_1-C_4$-alkoxy, which is optionally substituted by 1 to 5 fluorine and/or chlorine atoms, or $C_1-C_4$-alkylthio, which is optionally substituted by 1 to 5 fluorine and/or chlorine atoms or $C_1-C_4$-acyloxy, by $C_1-C_6$-alkoxy, $C_2-C_6$-alkenoxy or $C_2-C_6$-alkinoxy, where the alkoxy, alkenoxy or alkinoxy radicals are optionally substituted by 1 to 5 fluorine and/or chlorine atoms, by $C_1-C_6$-alkylthio, $C_2-C_6$-alkenylthio or alkinylthio, where the alkylthio, alkenylthio or alkinylthio radicals are optionally substituted by 1 to 5 fluorine and/or chlorine atoms, by $(C_1-C_6\text{-alkyl})$carbonyloxy, which is optionally substituted by 1 to 5 fluorine and/or chlorine atoms, by amino, which is optionally substituted by 1 to 2 identical or different alkyl radicals with 1 to 6 carbon atoms, which are optionally substituted by 1 to 5 fluorine and/or chlorine atoms, by nitro or cyano, $Y^1$ represents chlorine or bromine and $Y^2$ represents chlorine or bromine or $C_1-C_5$-alkyl, which is optionally substituted identically or differently by 1 to 7 fluorine and/or chlorine atoms.

4. Process for preparing substituted 2-arylpyrroles of the general formula (I), in which $R^1$, $R^2$, $R^3$, $R^4$, Ar, $Y^1$ and $Y^2$ have the meaning given in claim 1, wherein 2-arylpyrroles of the formula (II)

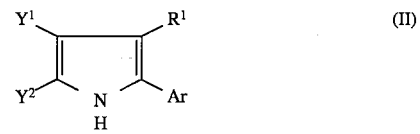

in which $R^1$, $Y^1$ and $Y^2$ have the abovementioned meaning, are reacted with compounds of the formula (III)

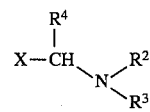

in which $R^2$, $R^3$ and $R^4$ have the abovementioned meaning and

X represents an anionic leaving group, optionally in the presence of bases and/or optionally in the presence of diluents.

5. A method for combating animal pests, wherein substituted 2-arylpyrroles of the formula (I) are allowed to act on animal pests and/or their habitat.

6. A pesticidal composition comprising a pesticidally-effective amount of at least one substituted 2-arylpyrrole according to claim 1, an extender or a surface-active agent, or both an extender and a surface-active agent.

* * * * *